United States Patent
Furukawa et al.

(10) Patent No.: US 7,332,475 B2
(45) Date of Patent: Feb. 19, 2008

(54) PREVENTIVE OR THERAPEUTIC COMPOSITION FOR VIRAL INFECTIOUS DISEASE

(75) Inventors: Satoru Furukawa, Tokyo (JP); Hideo Kawabe, Tokyo (JP); Hitoshi Ohori, Towada (JP); Takao Mukai, Towada (JP); Mitsuyo Matsumoto, Sendai (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 75 days.

(21) Appl. No.: 10/565,434

(22) PCT Filed: Jul. 22, 2004

(86) PCT No.: PCT/JP2004/010765

§ 371 (c)(1),
(2), (4) Date: Jan. 20, 2006

(87) PCT Pub. No.: WO2005/007640

PCT Pub. Date: Jan. 27, 2005

(65) Prior Publication Data

US 2006/0189542 A1    Aug. 24, 2006

(30) Foreign Application Priority Data

Jul. 22, 2003  (JP) ............... 2003-199593
Mar. 29, 2004  (JP) ............... 2004-093952

(51) Int. Cl.
*A61K 38/05*  (2006.01)
*A61K 38/00*  (2006.01)

(52) U.S. Cl. ............................................. 514/18; 514/2
(58) Field of Classification Search .................... None
See application file for complete search history.

(56) References Cited

U.S. PATENT DOCUMENTS 6,013,632 A * 1/2000 Jones et al. .................... 514/17
6,107,281 A * 8/2000 Jones et al. .................... 514/17

FOREIGN PATENT DOCUMENTS

| EP | 0 764 442 A1 | 3/1997 |
|---|---|---|
| JP | 1-265023 | 10/1989 |
| JP | 8-504799 | 5/1996 |
| JP | 2000-44473 | 2/2000 |
| JP | 2002-501901 | 1/2002 |
| JP | 2002-335926 | 11/2002 |
| JP | 2003-40792 | 2/2003 |
| WO | WO 94/14473 | 7/1994 |
| WO | WO 99/38522 | 8/1999 |
| WO | WO 02/09099 | 1/2002 |

OTHER PUBLICATIONS

Zhong, Chinese Medical Journal, 2003, vol. 116(6), pp. 803-804.*
Woong et al. 2003, DNA and Cell Biology, vol. 22(3), pp. 217-224.*
Saito et al. 2002, Microbiol. Immunol., vol. 46(4), pp. 249-255.*
Clark et al. 1998, Veterinary Microbiology, vol. 63, pp. 147-157.*
Holmes, Kathryn V., SARS coranavirus: a new challenge for prevention and therapy, the Journal of Clinical Investigation, Jun. 2003, vol. 111, No. 11, p. 1605-1609.
De Moerlooze, L., et al., Nucleotide sequence of the bovine viral diarrhea virus Osloss strain : comparison with related viruses and identification of specific DNA probes in the 5' untranslated region. Journal of General Virology, 1993, vol. 74, No. 7, p. 1433-1438.

* cited by examiner

*Primary Examiner*—B. Dell Chism
(74) *Attorney, Agent, or Firm*—Antonelli, Terry, Stout & Kraus, LLP.

(57) ABSTRACT

The invention provides a composition for preventing or treating infectious diseases of a virus belonging to the Coronavirus family or Flavivirus family, the composition containing one or more substances selected from reduced glutathione or oxidized glutathione or pharmaceutically acceptable salts thereof and catechin, and a composition for preventing or treating infectious diseases of a virus belonging to the Coronavirus family or Flavivirus family, the composition containing reduced glutathione or oxidized glutathione or pharmaceutically acceptable salts thereof and catechin.

9 Claims, 2 Drawing Sheets

PREVENTIVE OR THERAPEUTIC COMPOSITION FOR VIRAL INFECTIOUS DISEASE

TECHNICAL FIELD

The present invention relates to a composition for preventing or treating virus infectious diseases.

BACKGROUND ART

A coronavirus is an RNA virus with which humans, pigs, cow, chickens and the like are infected. In humans, the coronavirus has been long known as a causal virus of a cold along with an influenza virus. However, the coronavirus and the influenza virus are different in the following points.

That is, the coronavirus is a single-stranded plus chain RNA virus, while the influenza virus is a single-stranded minus chain RNA virus [refer to J. Virol., 29, 293-300 (1979), Am. J. Vet. Res., 37, 1031-41 (1976) and Virus, vol. 52, pp. 55-59, 2002]. Sialic acid molecular types of receptors that influenza viruses A and B and the coronavirus recognize are different [refer to J. Virol., 65, 6232-6273 (1991) and Virology, 189, 121-31 (1992)].

In case of the influenza virus, it has been reported that a host range is changed by substitution of one base of hemagglutinin (HA), one of spike sugar proteins present in a membrane, and it has been further known that attack from a host is escaped by changing an antigen via stimulation of an antibody pressure or the like (refer to Virus, vol. 51, pp. 193-200, 2001). Meanwhile, in case of the coronavirus, it has been considered that mutation easily occurs owing to a transcription process of a viral RNA described below.

The transcription processes of viral RNAs of the influenza virus and the coronavirus are different in the following points. Transcription of the viral RNA of the influenza virus takes place in a nucleus of a host cell, and the viral RNA synthesizes a viral template RNA by adding CAP present in a 5'-terminal region of an mRNA of the host cell to a 3'-terminal region of its own, like a primer [refer to J. Gen. Virol., 83, 723-34 (2002)]. Accordingly, it has been clarified that in the influenza virus, the mRNA synthesis on the host side is blocked with an inhibitor of an RNA polymerase such as actinomycin D or α-amanitinto inhibit its growth [refer to Philos Trans R. Soc. Lond. B Biol. Sci., 288, 359-70 (1980) and Arch. Virol., 141, 1587-94 (1996)].

On the other hand, transcription of the coronavirus takes place in a cytoplasm of a host cell. The detail of its process is unknown at present. However, it has been known that at least transcription using an mRNA of a host does not take place. Therefore, transcription is not inhibited, in most cases, with a drug such as actinomycin D or α-amanitin [Refer to Advances in virus research, 48, 1-100 (1997)].

Severe acute respiratory syndrome (hereinafter abbreviated as SARS) virus is a new coronavirus considered to be derived from wild animals. With respect to the number of patients of SARS induced by SARS virus, the number of infected persons in the whole world exceeds 8,439, and the number of the dead is 812 (as of Jul. 3, 2003). Thus, the mortality is high, and the countermeasure for treating or preventing the same is a global urgent necessity. It has been known that SARS virus can be destroyed with an bactericide or a disinfectant such as 75% alcohol. However, drugs effective for prevention or treatment of infection, including vaccines, have been unknown.

Glutathione is a tripeptide having a structure of γ-L-Glu-L-Cys-Gly, and it has been known as a therapeutic agent of acetonemia caused by an alcohol.

Glutathione has been known to have an effect for preventing or treating infectious diseases of the influenza virus which is different from the coronavirus in drug sensitivity (pamphlet of WO 98/30228). However, it has been unknown that glutathione has an effect for preventing or treating infectious diseases of the coronavirus.

Catechin is a water-soluble polyhydric phenol contained in a woody plant in large quantities, and it has been known to have a growth inhibitory activity of the influenza virus [refer to Planta medica, 67, 240-43 (2001)].

Anti-influenza nutrient foods containing glutathione and catechin have been also known (refer to JP-T-2001-511770 (the term "JP-T" as used herein means a published Japanese translation of a PCT patent application)). However, it has been unknown that a catechin-containing composition has an effect for preventing or treating coronavirus infectious diseases.

As a virus belonging to the Flavivirus family which is a single-stranded plus RNA virus, hog cholera virus (CSFV), bovine viral diarrhea virus (BVDV) and the like have been known. Especially BVDV is a virus which involves a serious problem in livestock industry as a virus that induces a hemorrhagic syndrome of high lethality with reduction of platelets. Nevertheless, an effective method for preventing BVDV infectious diseases has been unknown.

DISCLOSURE OF THE INVENTION

The invention aims to provide a composition effective for preventing or treating infectious diseases of a virus belonging to the Coronavirus family or Flavivirus family.

The invention relates to the following (1) to (15).

(1) A composition for preventing or treating infectious diseases of a virus belonging to the Coronavirus family or Flavivirus family, which comprises at least one member selected from the group consisting of reduced and oxidized glutathiones, pharmaceutically acceptable salts thereof and catechin.

(2) The composition according to (1), which comprises reduced or oxidized glutathione, or a pharmaceutically acceptable salt thereof, and catechin.

(3) The composition according to (1) or (2), which further comprises one or more antioxidants.

(4) The composition according to any one of (1) to (3), wherein the virus belonging to the Coronavirus family is severe acute respiratory syndrome (hereinafter abbreviated as SARS) virus.

(5) The composition according to any one of (1) to (3), wherein the virus belonging to the Flavivirus family is bovine viral diarrhea virus (hereinafter abbreviated as BVDV).

(6) The composition according to any one of (1) to (5), which is a pharmaceutical preparation.

(7) The composition according to (6), wherein the pharmaceutical preparation is an oral preparation, an injection solution, a nasal aerosol or an inhalant.

(8) The composition according to any one of (1) to (5), which is a food and drink, a feed, a food additive or a feed additive.

(9) A method for preventing or treating infectious diseases of a virus belonging to the Coronavirus family or Flavivirus family for non-human animals, which comprises administering the nasal aerosol as recited in (7) held at from 30° C. to 50° C. into the nose of non-human animals.

(10) The preventing or treating method of (9), wherein the virus belonging to the Coronavirus family is SARS virus.

(11) The method according to (9), wherein the virus belonging to the Flavivirus family is BVDV.

(12) Use of at least one member selected from the group consisting of reduced and oxidized glutathiones, pharmaceutically acceptable salts thereof and catechin for manufacture of a composition for preventing or treating infectious diseases of a virus belonging to the Coronavirus family or Flavivirus family.

(13) Use according to (12), wherein at least one member selected from the group consisting of reduced and oxidized glutathiones, pharmaceutically acceptable salts thereof and catechin are reduced or oxidized glutathione, or a pharmaceutically acceptable salt thereof, and catechin.

(14) A method for preventing or treating infectious diseases of a virus belonging to the Coronavirus family or Flavivirus family, which comprises administering at least one member selected from the group consisting of reduced and oxidized glutathiones, pharmaceutically acceptable salts thereof and catechin.

(15) The method according to (14), which comprises administering reduced or oxidized glutathione, or a pharmaceutically acceptable salt thereof, and catechin.

In the present invention, the reduced glutathione means a tripeptide having a structure of γ-L-Glu-L-Cys-Gly, and the oxidized glutathione means a glutathione dipeptide in which two molecules of reduced glutathione are bound via an S-S bond.

The reduced and oxidized glutathiones used in the present invention can be obtained by any conventional methods. As the method for producing the reduced glutathione, mention may be made of an extraction method from microorganisms such as yeasts [Methods in Enzymology, 3, 603 (1957), a chemical synthesis method [Bull. Chem. Soc. Jpn., 53, 2529 (1980)], an enzyme method (Japanese published unexamined patent application no. 74595/86) and the like. The oxidized glutathione can be obtained according to the method described in Acta Biochim. Pol., 17, 175 (1970).

Among from the methods for producing the reduced glutathione, the chemical synthesis method and the extraction method from yeasts are mentioned below.

1. Chemical Synthesis Method

The reduced glutathione can chemically be synthesized according to the method described in Bull. Chem. Soc. Jpn., 53, 2592 (1980).

Ethyl N-formyl-L-2-amino-4-cyanobutyrate is condensed with ethyl L-cysteinylglycinate to obtain (4R)-2-[(3S)-3-ethoxycarbonyl-3-(formylamino)propyl]-4-(ethoxycarbonylmethylcarbamoyl)-2-thiazoline. Subsequently, the resulting compound is saponified in an acetone aqueous solution at approximately −15° C., and treated with dilute sulfuric acid (pH 4) to obtain formylglutathione. Formylglutathione is then hydrolyzed with 0.5 mmol/l sulfuric acid to remove a formyl group and thus free glutathione is obtained. Free glutathione is further purified as required. In the further purification, free glutathione is converted into its copper thiolate which is then treated with hydrogen sulfite. In this manner, pure glutathione can be obtained.

2. Method for extraction of reduced glutathione from yeasts

The reduced glutathione can be extracted from yeasts according to the method described in Methods in Enzymology, 3, 603 (1957).

To a yeast extract, an equal amount of 10% trichloroacetic acid (TCA) is added. A residue obtained by centrifugation is further treated twice with half of the original volume of TCA. The extracts are combined, and a cadmium chloride solution is added in a volume which is ¼ the volume of the extract. The pH of the solution is adjusted to 5 by addition of 10 mol/l sodium hydroxide, and then to 6.5 with a bicarbonate salt. A cadmium complex precipitated is retained at 0° C. for 1 hour, and then washed twice with ice-cooled distilled water. After the precipitate is dissolved in sulfuric acid in a minimal amount of 2 mol/l, 0.5 mol/l sulfuric acid is added in an amount of 3 ml per 10 mg as an expected amount of glutathione to be obtained. As required, the solution is filtered, and the existing amount of glutathione is measured in terms of an aliquot unit. The solution is warmed at 40° C., and a copper oxide suspension containing copper oxide in an amount of 2.5 mg per 10 mg of glutathione is added dropwise while being gently shaken. The resulting precipitate is allowed to stand at 0° C. for some hours, centrifuged, and washed twice with 0.5 mol/l sulfuric acid, three times with distilled water and twice with methanol in this order. For isolating free glutathione, a copper complex of glutathione is decomposed with hydrogen in an aqueous suspension, and a solution obtained after removal of copper sulfite is dried by freeze-drying.

Regarding catechin in the present invention, any substance containing catechin selected from epicatechin, catechin, epigallocatechin, gallocatechin, epicatechin gallate and epigallocatechin gallate (hereinafter abbreviated as EGCg) either singly or in combination thereof in any amount is available. Catechin used in the present invention may be a commercially available product or a substance obtained by extraction from an organism containing catechin. As the organism containing catechin, for example, plants are mentioned, and tea leaf plants and the like are preferable. As catechin extracted from the organism, a purified product is available, and a crude extract is also available so long as catechin is contained therein to such an extent that the effect of the present invention is exhibited.

Examples of an extraction method and a purification method of catechin can include a method in which green leaves are extracted with water, caffeine is removed with chloroform and extraction is conducted with ethyl acetate (Chagyo Kenkyu Hokoku No. 13, p. 4, Apr. 1959), a method in which caffeine is removed from a tea extract with hexane and chloroform and desired tea catechins are extracted with ethyl acetate (Japanese published unexamined patent application no. 9922/89), a method for producing tea catechins including a catechin polymer or composite in which a multi-stage batch process allowing high-load conditions is conducted with gel beads using a substance extracted from a plant such as a tea tree with a lower alcohol aqueous solution as a raw material (Japanese published unexamined patent application no. 14572/91), a method in which a tea extract obtained by extracting tea leaves with hot water is used as a raw material, an adsorbent is filled in a chromatographic column, and tea catechins are selectively adsorbed on this adsorbent and recovered by elution with a hydrophilic organic solvent to prepare high-purity tea catechins (Japanese published unexamined patent application no. 311474/90), and the like.

The composition of the present invention may be either a composition comprising reduced or oxidized glutathione, a pharmaceutically acceptable salt thereof or catechin solely, or a composition comprises reduced or oxidized glutathione, or a pharmaceutically acceptable salt thereof, and catechin.

When the composition of the present invention contains reduced or oxidized glutathione or pharmaceutically acceptable salt thereof, one substance selected from reduced and oxidized glutathiones, and pharmaceutically acceptable salts thereof may be contained, or alternatively reduced glutathione, oxidized glutathione and pharmaceutically acceptable salts thereof may be contained in an arbitrary combination.

Examples of pharmaceutically acceptable salts (in the form of a water-soluble, oil-soluble or dispersible product) of reduced and oxidized glutathiones include usual non-toxic salts made of inorganic acids, organic acids or bases, and quaternary ammonium salts and the like. Examples of the salts made of inorganic acids or organic acids include acetate, adipate, arginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, piclate, pivalate, propionate, succinate, tartrate, thiocyanate, tosylate, undecanoate and the like. Examples of the salts made of bases include alkali metal salts such as an ammonium salt, a sodium salt and a potassium salt, alkaline earth metal salts such as a calcium salt and a magnesium salt, salts with organic bases such as a dicyclohexylamine salt and an N-methyl-D-glucamine salt, and salts with amino acids such as arginine and lysine, and the like.

Examples of the quaternary ammonium salts include salts obtained by quaternization with compounds, for example, lower alkyl halides such as chlorides, bromides and iodides of methyl, ethyl, propyl and butyl, dialkyl sulfates such as dimethyl sulfate, diethyl sulfate and dibutyl sulfate, diamyl sulfate, long-chain halides such as chlorides, bromides and iodides of decyl, lauryl, myristyl and stearyl, and aralkyl halides such as benzyl bromide and phenetyl bromide, and the like. Other pharmaceutically acceptable salts include a sulfate salt ethanolate and a sulfate salt.

As the antioxidant to be contained in the composition of the present invention, a substance selected from the group consisting of vitamin A, vitamin E, vitamin K, copper (copper (II) oxide), zinc (zinc oxide), iron (ferrous salt), selenium (sodium selenate), β-carotene, polyphenols, flavinoids, flavanols such as quercetin, flavanones such as eriodictyol, diterpenoids such as carnosinic acid and carnosol, phenolic acids such as rosemaric acid, caffeic acid, cumaric acid, cinnamic acid, coenzyme Q10, probucol, carotenoids such as astaxanthin and lycopin, α-lipoate and uric acid salt can be mentioned.

Examples of the virus belonging to the Coronavirus family in the present invention include SARS virus, chicken coronavirus, human cold coronavirus, bovine corona coronavirus and the like.

Examples of the virus belonging to the Flavivirus family in the present invention include yellow fever virus, dengue virus, hog cholera virus, BVDV, Border disease virus and the like.

The composition in the present invention can be used as a pharmaceutical preparation, a food, a feed, a food additive and a feed additive.

Examples of the pharmaceutical preparation include an oral preparation, a mouth wash or gargle preparation, a nasal aerosol, an inhalant, drops, an injection solution for intravenous injection or intramuscular injection, a suppository and the like.

The oral preparation can be prepared by any method well known in the technical field of pharmacology upon mixing one or more substances selected from reduced and oxidized glutathiones, pharmaceutically acceptable salts thereof (hereinafter abbreviated as glutathione) and catechin with a carrier as required.

When making the oral preparation, additives such as an excipient, a binder, a disintegrant, a lubricant, a dispersing agent, a suspending agent, an emulsifier, a diluting agent, a buffering agent, an antioxidant and an antibacterial agent can be used.

Examples of the dosage form of the oral preparations include tablets, powders, granules, emulsions, syrup, capsules and the like. For example, when the dosage form of the oral preparations is tablets, powders, granules or the like, the preparations can be prepared by adding excipients, for example, sugars such as lactose, white sugar, glucose, sucrose, mannitol and sorbitol, starches such as potato starch, wheat starch and corn starch, inorganic substances such as calcium carbonate, calcium sulfate, sodium hydrogencarbonate and sodium chloride and plant powders such as licorice powder and gentian powder, disintegrants such as starch, agar, gelatin powder, crystalline cellulose, carmellose sodium, carmellose calcium, calcium carbonate, sodium hydrogencarbonate and sodium alginate, lubricants such as magnesium stearate, talc, hydrogenated vegetable oil, macrogol and silicone oil, binders such as polyvinyl alcohol, hydroxypropyl cellulose, methyl cellulose, ethyl cellulose, carmellose, gelatin and starch paste, surfactants such as fatty acid esters, plasticizers such as glycerin, and the like.

When the dosage form of the oral preparation is a liquid preparation such as an emulsion or syrup, the preparation can be prepared by adding water, sugars such as sucrose, sorbitol and fructose, glycols such as polyethylene glycol and propylene glycol, oils such as sesame oil, olive oil and soybean oil, antiseptics such as p-hydroxybenzoate esters, flavors such as strawberry flavor and peppermint, and the like. Any concentrations of glutathione and catechin in the liquid preparation are available. The concentration of glutathione can be preferably from 10 mmol/l to 200 mmol/l, more preferably from 20 to 50 mmol/l. The concentration of catechin can be preferably from 10 µmol/l to 10 mmol/l, more preferably from 20 µmol/l to 2 mmol/l. Any pH of the liquid preparation is available so long as one or more substrates selected from glutathione and catechin are stable and its range can be preferably from 4.0 to 6.0.

When the dosage form of the oral preparation is a capsule, it can be prepared by filling the composition in a hard capsule or coating the composition with a capsule base to form a soft capsule. As the capsule base, gelatin can be mentioned. In the soft capsule, glycerin or sorbitol is added for imparting plasticity. Further, it is possible to add, as required, dyes, light-shielding agents such as titanium oxide, barium sulfate and precipitated calcium carbonate and antiseptics such as p-oxybenzoate esters.

When the composition of the present invention is administered to humans as an oral preparation for medical use, the dose and the administration schedule vary depending on the mode of administration, the age and body weight of a patient, the symptom and the like. It is usually from 1 mg to 10,000 mg, preferably from 20 to 2,000 mg, more preferably from 50 to 500 mg as glutathione. It is usually from 1 µg to 500 mg, preferably from 20 µg to 100 mg, more preferably from 50 µg to 25 mg as catechin. It is administered once to several times a day.

The mouth wash or gargle preparation can be prepared by adding an antimicrobial agent, a surfactant, a co-surfactant, oil, water and other additives, a sweetener/corrigent known in the technical field of preparations, and the like to one or more substances selected from glutathione and catechin.

Any concentrations of glutathione and catechin contained in the mouth wash or gargle preparation are available. The concentration of glutathione can be preferably from 10 mmol/l to 200 mmol/l, more preferably from 20 to 50 mmol/l. The concentration of catechin can be preferably from 10 nmol/l to 10 mmol/l, more preferably from 20 μmol to 2 mmol/l. Any pH of the liquid preparation is available so long as one or more substrates selected from glutathione and catechin are stable and its range can be preferably from 4.0 to 6.0.

The nasal aerosol or the inhalant can be prepared in the form of a physiological saline solution by a method well known in the technical field of pharmaceutical preparations using appropriate preservatives such as benzyl alcohol, absorption accelerators for increasing bioavailability, fluorocarbons, other dissolving agents or dispersing agents well known in the technical field, surfactants, gelling agents, buffering agents and other stabilizers and solubilizing agents [Pharmaceutical Dosage Forms and Drug Delivery Systems, 6th edition (1995)].

A method for making preparations in the intranasal administration (intranasal administration preparations) is known to those skilled in the art, and a part thereof has been described in Remington's Pharmaceutical Sciences, 17th edition (1985) which is a standard document in the technical field.

With respect to the carrier used in the intranasal administration preparation, any carrier which can be used in the preparations is available. It can be selected depending on a desired intranasal dosage form such as a solution, a suspension, an ointment or a gel. The intranasal administration preparation generally contains an active ingredient and further a large amount of water. Small amounts of other components may be contained, examples thereof including a pH adjustor, an emulsifier, a dispersing agent, a preservative, a surfactant, a gelling agent, a buffering agent, a stabilizer and a solubilizing agent. The intranasal administration preparation is preferably isotonic to an intranasal secretion.

The intranasal administration preparation can be prepared in the intranasal dosage form such as drops, a spray agent or aerosol. In the administration system, administration is possible in terms of a unit administration system as required. A volume of a solution or a suspension to be administered for a unit dose is preferably from 5 to 400 μl, more preferably from 50 to 150 μl.

In the administration system of the administration preparation described above, a dropper bottle, a plastic squeezer, an atomizer, a nebulizer or a medical aerosol (unit dose or plural-dose package) can be used.

When the composition of the invention is administered to humans as a nasal aerosol or an inhalant, the concentration of glutathione in the preparation is preferably from 10 to 50 mmol/l, and the concentration of catechin is preferably from 10 μmol to 2 mmol/l. The administration schedule of the preparation varies depending on the mode of administration, the age and body weight of a patient, the symptom and the like. It is usually administered once to several times a day.

The temperature of the nasal aerosol in the intranasal administration of the nasal aerosol can be from 30 to 50° C., preferably from 35 to 40° C., more preferably 37° C.

Drops and an injection solution for intravenous or intramuscular injection can be prepared by an arbitrary method well known in the technical field of pharmacology upon dissolving one or more substances selected from glutathione and catechin in an aqueous solvent.

Drops or an injection solution can be prepared using additives such as an aqueous solvent, a non-aqueous solvent, a preservative, a stabilizer, a soothing agent, an isotonic agent, a buffering agent and an excipient.

Examples of the aqueous solvent include water for injection, a physiological saline solution, a Ringer's solution and the like. Examples of the non-aqueous solvent include vegetable oils such as peanut oil, sesame oil, corn oil, olive oil and cottonseed oil. Examples of the preservative include phenol, cresol and the like. Examples of the stabilizer include sulfite, sodium pyrosulfite, ascorbic acid and the like. Examples of the soothing agent include benzyl alcohol, chlorobutanol and the like. Examples of the isotonic agent include sodium chloride, glucose and the like. Examples of the buffering agent include citrate, acetate, phosphate and the like. Examples of the excipient include sorbitol and the like.

When the composition of the present invention is administered to humans as drops or an injection solution, the dose and the administration schedule vary depending on the mode of administration, the age and body weight of a patient, the symptom and the like. It is usually from 1 to 10,000 mg, preferably from 20 to 2,000 mg, more preferably from 50 to 500 mg as glutathione. It is usually from 1 μg to 500 mg, preferably from 20 μg to 100 mg, more preferably from 50 μg to 20 mg as catechin. It is administered once to several times a day.

In the administration system of the various dosage forms described above, a dropper bottle, a plastic squeezer, an atomizer, a nebulizer or a medical aerosol (unit dose or plural-dose package) can be used.

The suppository can be prepared by mixing one or more substances selected from glutathione and catechin with an appropriate non-irritant excipient which is solid at room temperature but is liquefied or dissolved in the rectal cavity to release a drug, such as cocoa butter, synthetic glyceride ester or polyethylene glycol.

The food additive of the present invention can be prepared by the same method as in case of the foregoing oral preparations. The food additive is processed and produced in the form of, for example, powders, granules, pellets, tablets or various liquid preparations usually by adding or dissolving other food additives as required.

As the food and drink of the present invention, those containing one or more substances selected from glutathione and catechin can be mentioned.

The food and drink of the present invention can be processed and produced using general methods for production of foods and drinks except that one or more substances selected from glutathione and catechin are added to the food and drink.

The food and drink of the present invention can be produced by using, for example, granulating methods such as fluidized bed granulation, stirring granulation, extrusion granulation, rolling granulation, air stream granulation, compression molding granulation, crushing granulation, spray granulation and jet granulation, coating methods such as pan coating, fluidized bed coating and dry coating, puffing methods such as puff drying, excess vapor method, foam-mat method and microwave-heating method, and extrusion methods using an extrusion granulator, an extruder, or the like.

Examples of the food and drink of the present invention include juice, soft drinks, tea, dairy products such as lactic acid bacteria beverages, fermented milk, ice cream, butter, cheese, yogurt, processed milk and skim milk, meat products such as ham, sausage and hamburger, fish meat paste products such as kamaboko, chikuwa and satsumaage, egg products such as dashimaki and tamagodofu, confectionery such as cookies, jelly, chewing gum, candies, medicated candies and snacks, bread, noodles, pickles, smoked fish and meat, dried fish, tsukudani (food oiled down in soy), salted foods, soup and seasonings.

A medicated candy containing one or more substances selected from glutathione and catechin can be prepared according to U.S. Pat. No. 3,439,089.

The food and drink of the present invention may take the form of a powder food, a sheet-shaped food, a bottled food, a canned food, a retort pouched food, a capsule food, a tablet food, a liquid food, a nutritional drink or the like.

The food and drink of the present invention may be used as a health food, a functional food or the like for preventing or treating infectious diseases of a virus belonging to the Coronavirus family or Flavivirus family.

It is possible to add, to the food and drink or the food additive of the present invention, food additives generally used in foods and drinks, such as a sweetener, a coloring agent, a preservative, a thickening stabilizer, an antioxidant, a color developing agent, a bleaching agent, an antifungal agent, a gum base, a bitter agent, an enzyme, wax, a sour agent, a seasoning, an emulsifier, a nutrient supplement, a manufacture facilitating agent, a flavor and a spice extract.

The amount of one or more substances selected from glutathione and catechin to be added to the food and drink of the present invention or the amount of the food additive of the present invention to be added thereto is properly selected according to the type of the food and drink, the desired effect of injection of the food and drink, and the like. It is usually from 0.1 to 90% by weight, preferably from 1 to 70% by weight, especially preferably from 5 to 50% by weight as glutathione or catechin.

The ingestion amount of the food and drink of the present invention varies depending on the mode of ingestion, the age and body weight of the ingesting person and the like. It is usually from 100 to 10,000 mg, preferably from 100 to 2,000 mg, more preferably from 200 to 1,000 mg per adult per day as glutathione. It is usually from 100 µg to 500 mg, preferably from 100 µg to 100 mg, more preferably from 200 µg to 50 mg per adult per day as catechin. It is ingested at once or in several portions daily. Although the period of ingestion is not particularly limited, it is usually from one day to one year, preferably from one week to three months.

The feed additive of the present invention can be prepared by the same method as in case of the oral preparations of the present invention. The feed additive is processed and produced in the form of, for example, powders, granules, pellets, tablets or various liquid preparations usually by adding or dissolving other feed additives as required.

Examples of the feed additive can include the foregoing food additives which can be added to the food additive of the present invention, such as a sweetener, a coloring agent, a preservative, a thickening stabilizer, an antioxidant, a color developing agent, a bleaching agent, an antifungal agent, a gum base, a bitter agent, an enzyme, wax, a sour agent, a seasoning, an emulsifier, a nutrient supplement, a manufacture facilitating agent, a flavor and a spice extract.

The feed of the present invention can be used as a feed for preventing or treating infectious diseases of a virus belonging to the Coronavirus family or Flavivirus family to mammals or birds, for example, as a feed for livestock such as cow, horses and pigs and as a feed for poultry such as chickens and turkeys.

The feed of the present invention can be processed and produced by general methods for production of feeds except that one or more substances selected from glutathione and catechin or the feed additive of the present invention is added to the feed.

Examples of the feed include cereals, chaff and bran, vegetable oil cakes, feed derived from animals, other feeds, purified products, a mixture thereof and the like.

Examples of the cereals include milo, wheat, barley, oats, rye, unpolished rice, buckwheat, foxtail millet, common millet, Japanese millet, corn, soybean and the like.

Examples of the chaff and bran include rice bran, defatted rice bran, wheat bran, wheat middlings, wheat germ, barley bran, pellet, corn bran, corn germ and the like.

Examples of the vegetable oil cakes include soybean oil cake, soybean flour, linseed oil cake, cottonseed oil cake, peanut oil cake, safflower oil cake, coconut oil cake, palm oil cake, sesame oil cake, sunflower oil cake, rapeseed oil cake, kapok oil cake, mustard oil cake and the like.

Examples of the feeds derived from animals include fish meal such as northern ocean meal, imported meal, whole meal and coastal meal, fish soluble, meat meal, meat and born meal, blood powder, decomposed hair, bone meal, byproducts upon disposal of livestock, feather meal, silkworm pupa, skim milk powder, casein, dry whey and the like.

Examples of other feeds include stalks and leaves of plants such as alfalfa, hay cube, alfalfa leaf meal and powder of false acacia, byproducts in corn-processing industry, such as corn gluten, meal, corn gluten feed and corn steep liquor, processed starch products such as starch, fermentation industrial products such as yeast, beer cake, malt root, alcohol cake and soy sauce cake, byproducts in processing of agricultural products, such as processed citrus fruit cake, tofu (soybean curd) cake, coffee cake and cocoa cake, cassava, broad bean, guar meal, seaweeds, krill, spirulina, chlorella, minerals and the like.

Examples of the purified products include proteins such as casein and albumin, amino acids, starch, cellulose, sugars such as sucrose and glucose, minerals, vitamins and the like.

The feed of the present invention may also be produced by using, for example, granulating methods such as fluidized bed granulation, stirring granulation, extrusion granulation, rolling granulation, air stream granulation, compression molding granulation, crushing granulation, spray granulation and jet granulation, coating methods such as pan coating, fluidized bed coating and dry coating, puffing methods such as puff drying, excess vapor method, foam-mat method and microwave-heating method, extrusion methods using an extrusion granulator or an extruder, or the like.

The amount of one or more substances selected from glutathione and catechin or the feed additive to be added to the feed of the present invention is properly selected according to the type of the feed, the desired effect of ingestion of the feed and the like. It is usually from 0.001 to 100% by weight, preferably from 0.01 to 80% by weight, especially preferably from 0.1 to 60% by weight as glutathione or catechin.

The oral dose, namely the ingestion amount of the feed of the present invention varies depending on the mode of ingestion, the type, age and body weight of the ingesting animal, and the like. It is usually from 0.1 mg to 10 g, preferably from 1 mg to 5 g, more preferably from 10 mg to 1 g per kg of body weight per day for animals as glutathione. It is usually from 0.1 µg to 0.5 g, preferably from 1 µg to 0.25 g, more preferably from 10 µg to 0.5 g per kg of body weight per day for animals as catechin. It is ingested at once or in several portions daily. Although the ingestion period is not particularly limited, it is usually from one day to five years, preferably from two weeks to one year.

The growth inhibitory effect of glutathione to the virus belonging to the Coronavirus family is demonstrated in Test Example 1.

TEST EXAMPLE 1

Madin Darby Bovin Kidney (MDBK) cells (ATCC CCL-22) was incubated with a 48-well plate such that the cells were 90% confluent, and then washed twice with a phosphate buffered saline (PBS).

Each of bovine coronavirus (BCV) Kakegawa strain (procured from Nippon Zenyaku Kogyo Co., Ltd.) [2.56 to 256 hemagglutinin (HA) titer/25 µl] and Mebus strain (ATCC VR-874) (0.064 and 0.64 HA titers/25 µl) at various concentrations, these strains being diluted with fetal bovine serum (FBS)-free Minimum Essential Medium (MEM) [Science, 122, 501 (1952)], was inoculated in an amount of 200 µl/well, and incubated at 37° C. for 90 minutes while moving a plate at intervals of 15 minutes. After the culture solution was washed three times with PBS, 500 µl/well of 5% FBS-containing MEM containing 1, 5, 10, 20 or 30 mmol/l of reduced glutathione was added thereto, and the mixture was further incubated at 37° C. During the incubation, 100 µl of the supernatant was recovered in 24, 48, 72 and 96 hours to measure a hemagglutinin (HA) titer.

The HA titer was measured by adding 25 µl of PBS containing 0.03% BSA to each well, adding 25 µl of the BCV culture supernatant thereto by multiple dilution, adding 0.8% mouse immobilization red cells thereto and measuring an agglutination reaction of red cells after 3 hours.

Figure 1:
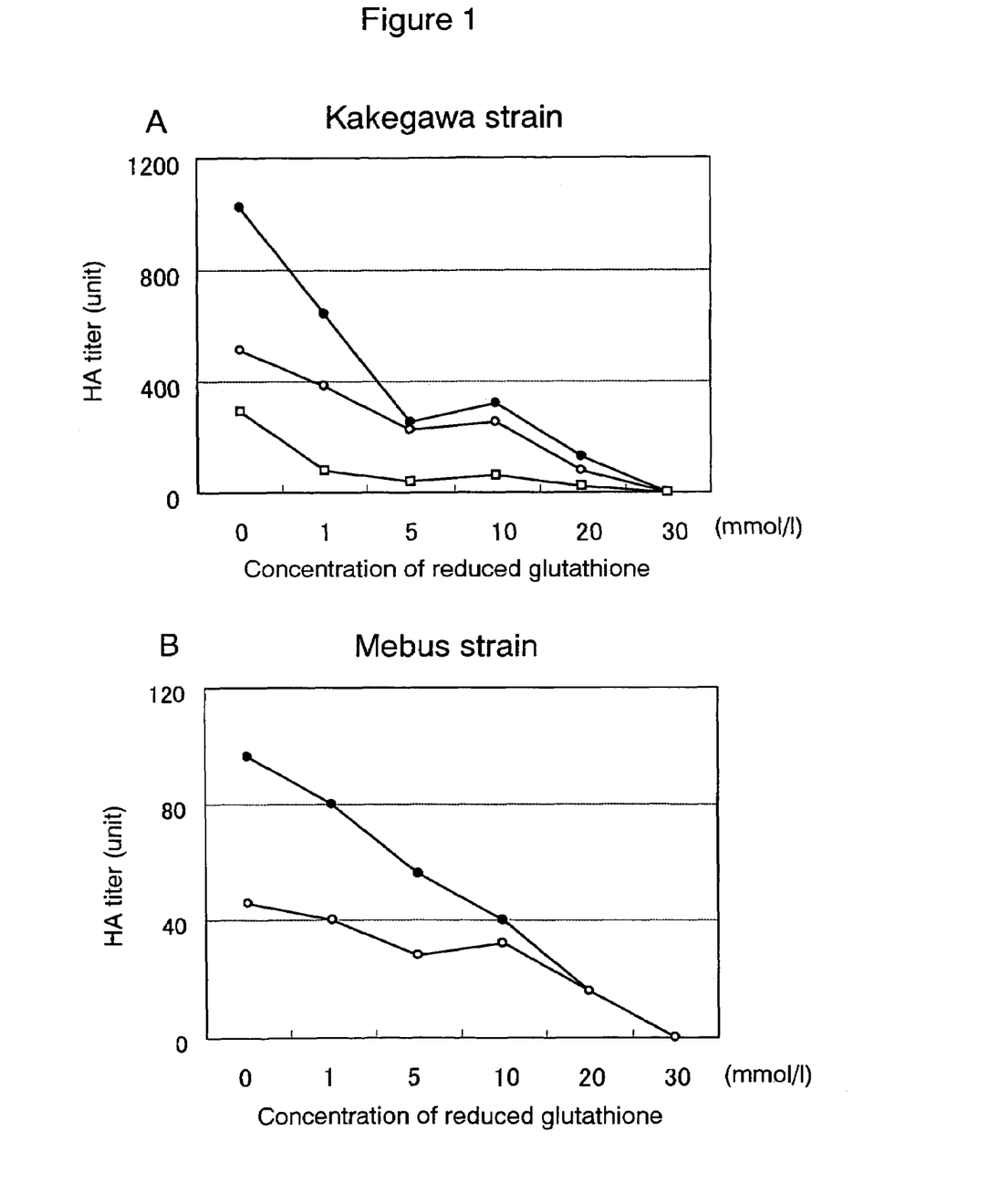
FIG. 1 is graphs showing effects of inhibiting growth of coronavirus by reduced glutathione. Graph A shows the results in case of using Kakegawa strain as BCV, and graph B shows the results in case of using Mebus strain as BCV. ★, ◢ and ◨ in graph A indicate the results of Kakegawa strains with 256 HA, 25.6 HA and 2.56 HA, respectively. ★ and ◢ in graph B indicate the results of Mebus strains with 0.64 HA and 0.064 HA, respectively. The abscissa axis of the graphs indicates the concentration of reduced glutathione, and the ordinate axis thereof indicates the hemagglutinin (HA) titer.

The results are shown in FIG. 1. Further, the results of measuring an HA titer over the course of time after addition of reduced glutathione are shown in FIG. 2.

Figure 2:
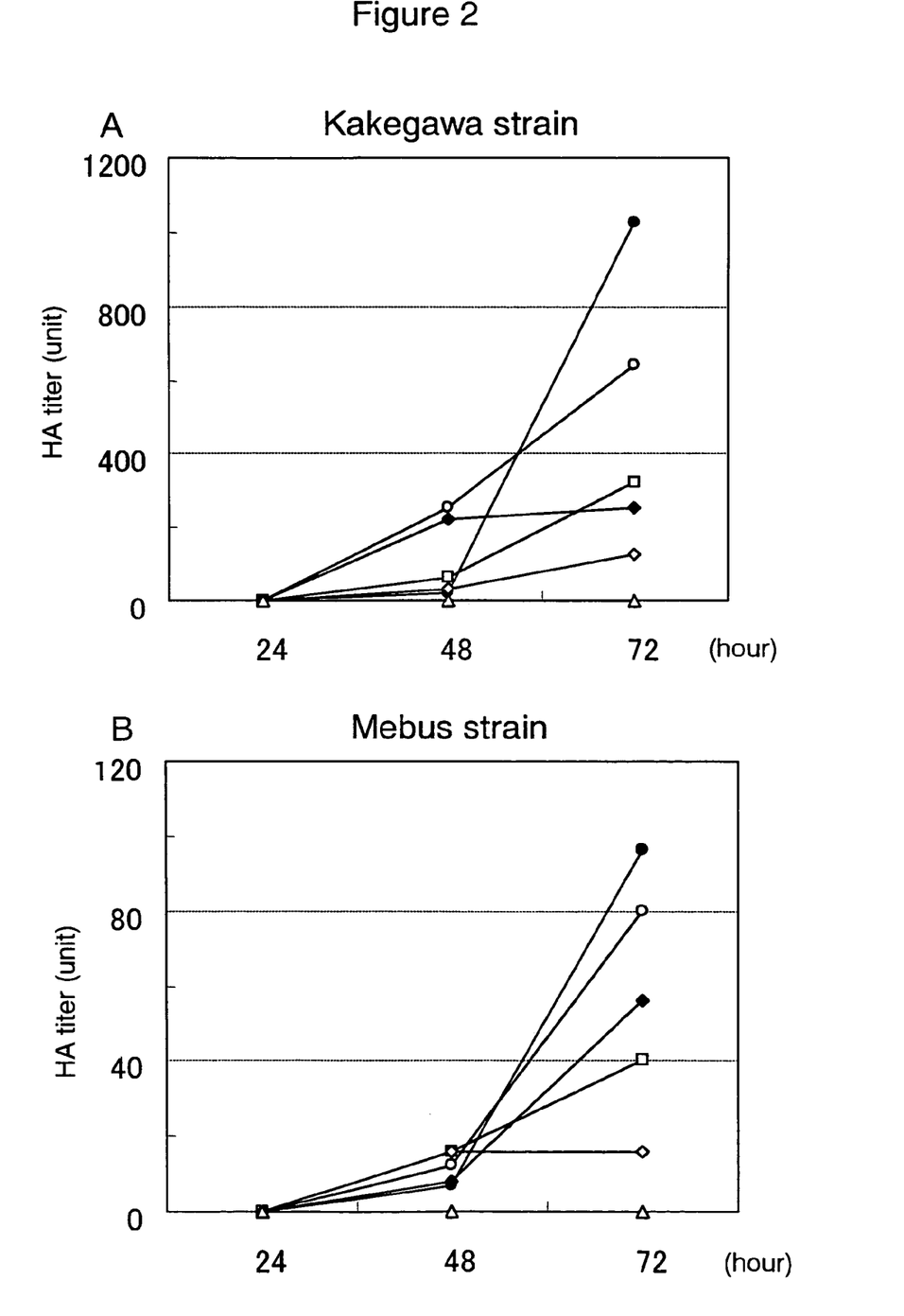
FIG. 2 is a graph showing an effect of inhibiting growth of coronavirus over the course of time by reduced glutathione. Graph A shows the results in case of using Kakegawa strain as BCV, and graph B shows the results in case of using Mebus strain as BCV. ★, ◢, ■, ◨, ♪, and ρ in the graphs indicate the results of reduced glutathione in amounts of 0, 1, 5, 10, 20 and 30 mmol/l, respectively. The abscissa axis of the graphs indicates the time that lapses from the contact of cells and coronavirus, and the ordinate axis thereof indicates the hemagglutinin (HA) titer.

FIGS. 1 and 2 reveal that reduced glutathione has an effect of inhibiting growth of coronavirus.

An effect of preventing virus infection by catechin is demonstrated in Test Examples 2 and 3 below.

TEST EXAMPLE 2

MDBK cells were incubated in a 48-well plate such that the cells were 90% confluent, and then washed twice with PBS.

BCV Kakegawa strain with a 50% tissue culture infectious dose ($TCID_{50}$) of $1.8 \times 10^8$/ml and 1 mg/ml of catechin (EGCg: procured from Pharma Foods International Co., Ltd.) were contacted at 25° C. or 37° C. for 30, 60 or 90 minutes respectively, and a 10-fold dilution series was then produced with MEM.

The virus dilute solution was inoculated in MDBK cells, and incubated at 37° C. for 90 minutes while moving a plate at intervals of 15 minutes. After the cells were washed three times with PBS, 5% FBS-containing MEM was added in an amount of 500 µl/well, and incubation was conducted for 72 hours. Subsequently, the cells infected with the virus were identified with a cell denaturation effect to measure $TCID_{50}$. The results are shown in Table 1.

TABLE 1

| Conditions | | $10^{(n)}$ $TCID_{50}$/ml | |
|---|---|---|---|
| Temperature | Contact time (min) | Control (without EGCg treatment) | EGCg-treated virus |
| 25° C. | 30 | 7.25 | 5.75 |
|  | 30 | 8.25 | 4.25 |
| 37° C. | 60 | 7.75 | <2.75 |
|  | 90 | 6.50 | <2.00 |

Table 1 reveals that catechin has an effect for preventing coronavirus infectious diseases.

TEST EXAMPLE 3

MDBK cells were incubated in a 48-well plate such that the cells were 90% confluent, and then washed twice with PBS.

BVDV(ATCC VR524) with $1.4 \times 10^5$ $TCID_{50}$/ml and 1 mg/ml of catechin (EGCg: procured from Pharma Foods International Co., Ltd.) were contacted at 37° C. for 30, 60 or 90 minutes, then inoculated in MDBK cells, and incubated for 90 minutes while moving a plate at intervals of 15 minutes. The cells were washed three times with PBS, and 5% FBS-containing MEM was added thereto. Incubation was further conducted at 37° C. for 6 days.

After completion of the incubation, a DNA derived from BVDV in the MDBK cells was detected by RT-PCR to confirm whether or not the cells were infected with the virus. Consequently, the BVDV-derived DNA became undetected depending on the catechin treatment time, and it was not detected at all in the experimental zone with the contact for 90 minutes.

The results reveal that catechin has an effect for preventing flavivirus infectious diseases.

Examples of the present invention are described below. However, the following Examples do not limit the scope of the present invention.

BEST MODE FOR CARRYING OUT THE INVENTION

EXAMPLE 1

Preparation of an Intranasal Spray Agent for Preventing or Treating Infectious Diseases of a Virus Belonging to the Coronavirus Family or Flavivirus Family An intranasal spray agent containing oxidized glutathione or reduced glutathione is prepared by adding and dissolving 3 mg of oxidized glutathione or reduced glutathione in 1 ml of a physiological saline solution [0.9% (w/v) sodium chloride aqueous solution].

An intranasal spray agent containing catechin is prepared by dissolving 3 mg of catechin in 1 ml of a physiological saline solution.

An intranasal spray agent containing oxidized glutathione or reduced glutathione and catechin is prepared by dissolving 3 mg of oxidized glutathione or reduced glutathione and 3 mg of catechin in 1 ml of a physiological saline solution.

EXAMPLE 2

Preparation of an Intranasal Spray Agent for Preventing or Treating Infectious Diseases of a Virus Belonging to the Coronavirus Family or Flavivirus Family (1)

A reduced glutathione-containing intranasal spray agent containing the following ingredients is prepared.

| | |
|---|---|
| Reduced glutathione | 1.0 g |
| Sodium acetate | 0.3 g |
| Methylparaben | 0.1 g |
| Propylparaben | 0.02 g |
| Sodium chloride | amount required for tension |
| Hydrochloric acid or sodium hydroxide | amount required for pH adjustment |
| Pure water | amount for adjusting a total volume to 100 ml |

A catechin-containing intranasal spray agent is prepared by using 1 g of catechin instead of reduced glutathione in the foregoing composition.

An intranasal spray agent containing reduced glutathione and catechin is prepared by adding 1 g of catechin to the foregoing composition.

EXAMPLE 3

Preparation of an Intranasal Spray Agent for Preventing or Treating Infectious Diseases of a Virus Belonging to the Coronavirus Family or Flavivirus Family (2)

An oxidized glutathione-containing intranasal spray agent containing the following ingredients is prepared.

| | |
|---|---|
| Oxidized glutathione | 1.0 g |
| Sodium acetate | 0.3 g |
| Methylparaben | 0.1 g |
| Propylparaben | 0.02 g |
| Sodium chloride | amount required for tension |
| Hydrochloric acid or sodium hydroxide | amount required for pH adjustment |
| Pure water | amount for adjusting a total volume to 100 ml |

An intranasal spray agent containing oxidized glutathione and catechin is prepared by adding 1 g of catechin to the foregoing composition.

EXAMPLE 4

Preparation of Drops for Preventing or Treating Infectious Diseases of a Virus Belonging to the Coronavirus Family or Flavivirus Family (1)

Reduced glutathione-containing drops are prepared using the following candy base and drug mixture.

| | |
|---|---|
| Candy base: | |
| Maltitol (medium grain size] | 35.0 kg |
| Corn syrup 43° Be | 21.0 kg |
| Drug mixture: | |
| Polyethylene glycol (molecular weight 6,000) | 2.75 kg |
| Reduced glutathione | 5.0 kg |
| Citric acid | 60.0 kg |
| Artificial wild cherry-like flavor | 60.0 g |

Preparation of the candy base is conducted as follows.

Maltitol is dissolved in 5.5 liters of water, glucose-containing corn syrup is added thereto, and they are fully mixed. At this time, any desired dye is added as required to give a desired color. A dye which can be dissolved well is used.

The mixture is charged into a steam jacket kettle heated at 125° C. From the kettle, the mixture is put into a storage container via a pump, and fed to a continuous cooker. While the syrup is passed through a coil of the cooker, the temperature reaches 125 to 150° C. The product is then fed to a receiving kettle kept in vacuum of 28 to 29 inches via a steam vacuum ejector for approximately 6 to 7 minutes. During this time, water is removed until the water content is reduced to approximately 1% or less to form an appropriate molten candy base. The molten candy base is slowly cooled to prepare a candy base.

Subsequently, reduced glutathione, citric acid and the artificial flavor (powder) are added to polyethylene to form a drug mixture. The mixture is then heated at approximately 90° C. for fluidization thereof. The resulting hot fluid mixture is rapidly added to the molten candy base (whose temperature is reduced to approximately 100° C. or a temperature slightly lower than that temperature) while they are properly mixed. The whole lump is then fully kneaded, and moved to a spinning machine. The resulting product is extruded to a lozenge forming die to prepare reduced glutathione-containing drops.

Catechin-containing drops are prepared by using 5.0 kg of catechin instead of reduced glutathione in the foregoing method.

Drops containing reduced glutathione and catechin are prepared by using 5.0 kg of catechin along with reduced glutathione in the foregoing method.

EXAMPLE 5

Preparation of Drops for Preventing or Treating Infectious Diseases of a Virus Belonging to the Coronavirus Family or Flavivirus Family (2)

The drug mixture-containing molten candy lump obtained in Example 4 is poured on a cooling table, solidified into a semi-solid lump on the cooling table, and then formed into any desired shape for ingesting a unit ingestion amount of reduced glutathione to prepare reduced glutathione-containing drops, catechin-containing drops or drops containing reduced glutathione and catechin.

EXAMPLE 6

Preparation of Drops for Preventing or Treating Infectious Diseases of a Virus Belonging to the Coronavirus Family or Flavivirus Family (3)

Oxidized glutathione-containing drops are prepared using the following candy base and drug mixture.

| Candy base: | |
|---|---|
| Maltitol (medium grain size] | 35.0 kg |
| Corn syrup 43° Be | 21.0 kg |

| Drug mixture: | |
|---|---|
| Polyethylene glycol (molecular weight 6,000) | 2.75 kg |
| Oxidized glutathione | 5.0 kg |
| Citric acid | 60.0 kg |
| Artificial wild cherry-like flavor | 60.0 g |

Preparation of the candy base is conducted as follows.

Maltitol is dissolved in 5.5 liters of water, glucose-containing corn syrup is added thereto, and they are fully mixed. At this time, any desired dye is added as required to give a desired color. A dye which can be dissolved well is used.

The mixture is charged into a steam jacket kettle heated at 125° C. From this kettle, the mixture is put into a storage container via a pump, and fed to a continuous cooker. While the syrup is passed through a coil of the cooker, the temperature reaches 125 to 150° C. The product is then fed to a receiving kettle kept in vacuum of 28 to 29 inches via a steam vacuum ejector for approximately 6 to 7 minutes. During this time, water is removed until the water content is reduced to approximately 1% or less to form an appropriate molten candy base. The molten candy base is slowly cooled to prepare a drop base.

Subsequently, oxidized glutathione, citric acid and the artificial flavor (powder) are added to polyethylene glycol to form a drug mixture. The mixture is then heated at approximately 90° C. to fluidize it. The resulting hot fluid mixture is rapidly added to the molten candy base (whose temperature is reduced to approximately 100° C. or a temperature slightly lower than that temperature) while they are properly mixed. The whole lump is then fully kneaded, and moved to a spinning machine. The resulting product is extruded to a lozenge forming dye to prepare oxidized glutathione-containing drops.

Catechin-containing drops are prepared by using 5.0 kg of catechin instead of oxidized glutathione in the foregoing method.

Drops containing oxidized glutathione and catechin are prepared by using 5.0 kg of catechin along with oxidized glutathione in the foregoing method.

EXAMPLE 7

Preparation of Drops for Preventing or Treating Infectious Diseases of a Virus Belonging to the Coronavirus Family or Flavivirus Family (4)

The drug mixture-containing molten candy lump obtained in Example 6 is poured on a cooling table, and solidified into a half-solid lump on the cooling table. The lump is then formed into any desired shape for ingesting a unit ingestion amount of oxidized glutathione to prepare drops containing oxidized glutathione, catechin, or oxidized glutathione and catechin.

INDUSTRIAL AVAILABILITY

The present invention provides a composition for preventing or treating infectious diseases of a virus belonging to the Coronavirus family or the Flavivirus family, which comprises at least one member selected from the group consisting of reduced and oxidized glutathiones, pharmaceutically acceptable salts thereof and catechin.

The invention claimed is:

1. A method for treating infectious diseases of a virus belonging to the Coronavirus family or Flavivirus family for non-human animals, which comprises administering a nasal aerosol comprising at least one member selected from the group consisting of reduced and oxidized glutathiones, and pharmaceutically acceptable salts thereof, held at from 30° C. to 50° C. into the nose of non-human animals.

2. The method according to claim 1, wherein the virus belonging to the Coronavirus family is severe acute respiratory syndrome (hereafter abbreviated as SARS) virus.

3. The method according to claim 1, wherein the virus belonging to the Flavivirus family is bovine viral diarrhea virus (hereinafter abbreviated as BVDV).

4. A method for treating infectious diseases of a virus belonging to the Coronavirus family or Flavivirus family, which comprises administering at least one member selected from the group consisting of reduced and oxidized glutathiones, pharmaceutically acceptable salts thereof.

5. A method for treating infectious diseases of a virus belonging to the Coronavirus family or Flavivirus family, which comprises administering reduced or oxidized glutathione, or a pharmaceutically acceptable salt thereof, and catechin.

6. The method according to claim 4, wherein the virus belonging to the Coronavirus family is SARS virus.

7. The method according to claim 4, wherein the virus belonging to the Flavivirus family is BVDV.

8. The method according to claim 5, wherein the virus belonging to the Coronavirus family is SARS virus.

9. The method according to claim 5, wherein the virus belonging to the Flavivirus family is BVDV.

* * * * *